United States Patent
Kameishi et al.

(10) Patent No.: US 11,109,844 B2
(45) Date of Patent: Sep. 7, 2021

(54) ULTRASOUND DIAGNOSIS APPARATUS AND ULTRASOUND PROBE

(71) Applicant: Toshiba Medical Systems Corporation, Otawara (JP)

(72) Inventors: Wataru Kameishi, Nasushiobara (JP); Makoto Hirama, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 478 days.

(21) Appl. No.: 15/271,788

(22) Filed: Sep. 21, 2016

(65) Prior Publication Data

US 2017/0086799 A1     Mar. 30, 2017

(30) Foreign Application Priority Data

Sep. 25, 2015   (JP) .............................. JP2015-188810
Sep. 12, 2016   (JP) .............................. JP2016-177643

(51) Int. Cl.
    *A61B 8/00*     (2006.01)
    *G01S 7/52*     (2006.01)
    *A61B 8/08*     (2006.01)

(52) U.S. Cl.
    CPC .............. *A61B 8/58* (2013.01); *A61B 8/5207* (2013.01); *A61B 8/54* (2013.01); *G01S 7/52017* (2013.01); *A61B 8/587* (2013.01)

(58) Field of Classification Search
    CPC ........... A61B 8/58; A61B 8/5207; A61B 8/54; A61B 8/587; G01S 7/52017
    See application file for complete search history.

(56) References Cited

U.S. PATENT DOCUMENTS 5,876,341 A  *  3/1999  Wang .................... G01S 7/5205
                                                  600/441
6,146,330 A  *  11/2000  Tujino ................ G01S 7/52038
                                                  600/443

(Continued)

FOREIGN PATENT DOCUMENTS

JP          10-14921        1/1998
JP          2006-217944     8/2006

(Continued)

*Primary Examiner* — Bill Thomson
*Assistant Examiner* — Younhee Choi
(74) *Attorney, Agent, or Firm* — Oblon, McClelland, Maier & Neustadt, L.L.P.

(57) ABSTRACT

An ultrasound diagnosis apparatus according to an embodiment includes an ultrasound probe and transmitter circuitry. The ultrasound probe is connected to a body through a cable and includes an ultrasound transducer element to transmit and receive an ultrasound wave. The transmitter circuitry generates transmission waveform data, generates, from the generated transmission waveform data, transmission signals that the ultrasound probe uses for transmitting ultrasound waves, and outputs the generated transmission signals to the ultrasound probe. When causing the ultrasound probe to transmit a plurality of ultrasound waves with different phases successively depending on a transmission condition, the transmitter circuitry generates transmission waveform data based on which a sum component of the ultrasound waves transmitted successively is within a certain range, by using the transmission signals detected between the cable and the ultrasound transducer element.

18 Claims, 6 Drawing Sheets

(56) References Cited

U.S. PATENT DOCUMENTS

| | | | | |
|---|---|---|---|---|
| 6,213,947 | B1* | 4/2001 | Phillips | G01S 7/52038 |
| | | | | 600/443 |
| 6,458,084 | B2* | 10/2002 | Tsao | G01S 7/52038 |
| | | | | 600/443 |
| 6,770,031 | B2* | 8/2004 | Hynynen | A61B 8/0858 |
| | | | | 600/437 |
| 7,479,110 | B2* | 1/2009 | Nishigaki | G10K 11/341 |
| | | | | 600/443 |
| 9,126,270 | B2* | 9/2015 | Nishio | A61B 17/1631 |
| 2005/0148874 | A1* | 7/2005 | Brock-Fisher | G01S 7/52049 |
| | | | | 600/447 |
| 2011/0098568 | A1* | 4/2011 | Someda | G01S 7/52049 |
| | | | | 600/443 |
| 2011/0237953 | A1* | 9/2011 | Olsson | G01S 7/5208 |
| | | | | 600/459 |
| 2015/0289849 | A1* | 10/2015 | Taniguchi | A61B 8/5207 |
| | | | | 600/443 |
| 2016/0120516 | A1* | 5/2016 | Imagawa | A61B 8/08 |
| | | | | 600/459 |

FOREIGN PATENT DOCUMENTS

| | | | |
|---|---|---|---|
| JP | 2006217944 A | * | 8/2006 |
| JP | 5247958 | | 7/2013 |

\* cited by examiner

ULTRASOUND DIAGNOSIS APPARATUS AND ULTRASOUND PROBE

CROSS-REFERENCE TO RELATED APPLICATIONS

This application is based upon and claims the benefit of priority from Japanese Patent Application No. 2015-188810, filed on Sep. 25, 2015, and Japanese Patent Application No. 2016-177643, filed on Sep. 12, 2016; the entire contents of which are incorporated herein by reference.

FIELD

Embodiments described herein relate to an ultrasound diagnosis apparatus and an ultrasound probe.

BACKGROUND

There has been a method for visualization in which a plurality of ultrasound waves with different phases are transmitted successively and nonlinear components (for example, harmonic components such as second harmonic components) contained in reception signals are used. In this method, for example, two ultrasound waves having an identical amplitude and inversed phases are transmitted successively for each scan line, and two reception signals received in this process are added. This addition processing cancels out fundamental components, and provides a signal mainly containing second harmonic components generated in a second nonlinear propagation. This signal is used to visualize the second harmonic components.

DETAILED DESCRIPTION

The following describes an ultrasound diagnosis apparatus and an ultrasound probe according to embodiments with reference to the drawings. The embodiments are not limited to the embodiments described below. The content of one embodiment is basically applied to another embodiment as well.

An ultrasound diagnosis apparatus according to an embodiment includes an ultrasound probe and transmitter circuitry. The ultrasound probe is connected to a body through a cable and includes an ultrasound transducer element to transmit and receive an ultrasound wave. The transmitter circuitry generates transmission waveform data, generates, from the generated transmission waveform data, transmission signals that the ultrasound probe uses for transmitting ultrasound waves, and outputs the generated transmission signals to the ultrasound probe. When causing the ultrasound probe to transmit a plurality of ultrasound waves with different phases successively depending on a transmission condition, the transmitter circuitry generates transmission waveform data based on which a sum component of the ultrasound waves transmitted successively is within a certain range, by using the transmission signals detected between the cable and the ultrasound transducer element.

First Embodiment

Figure 1:
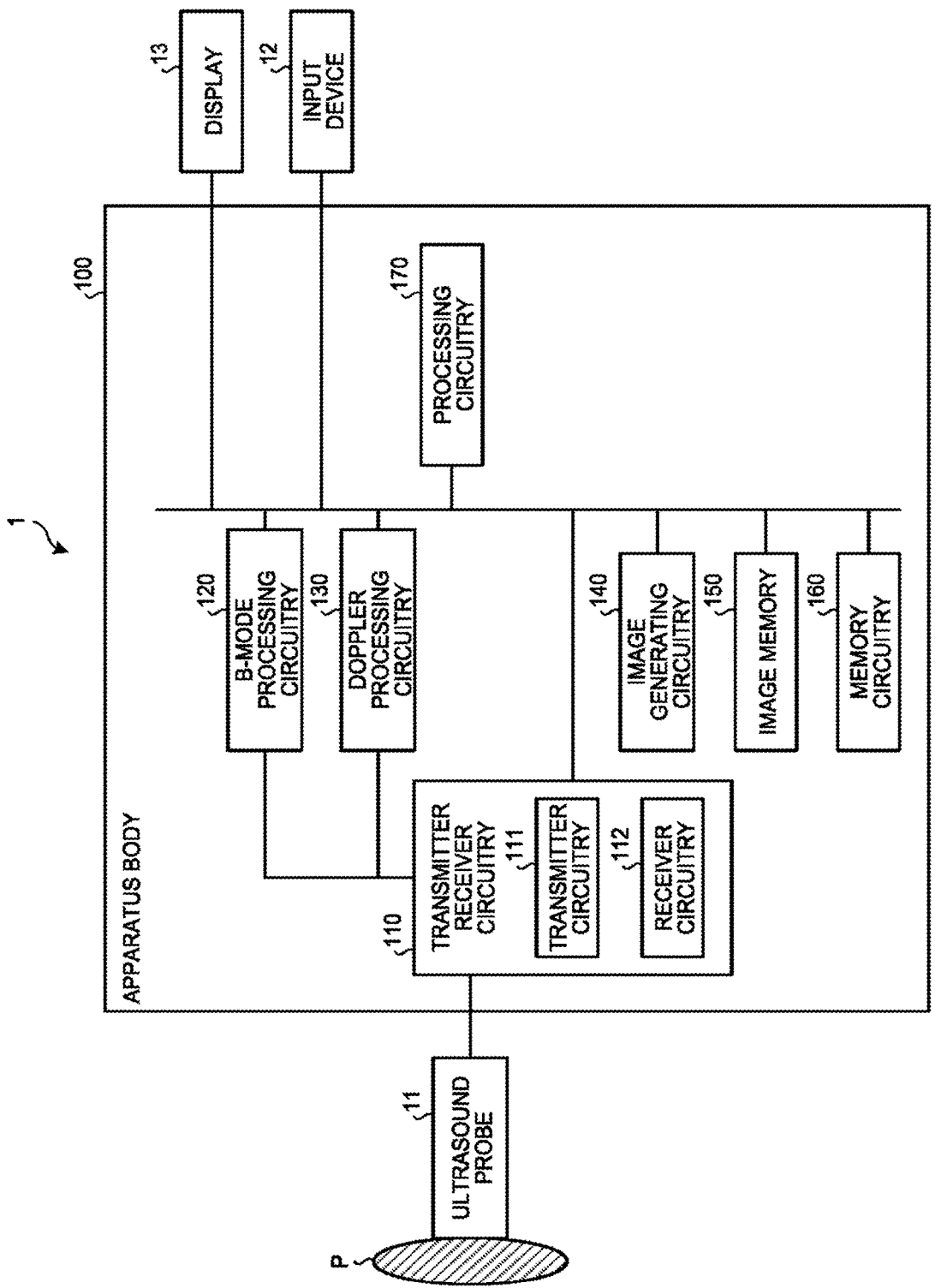
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an ultrasound probe 11, an input device 12, a display 13, and an apparatus body 100. The ultrasound probe 11 is communicably connected to transmitter receiver circuitry 110 described later, which is included in the apparatus body 100. The input device 12 and the display 13 are communicably connected to various circuits included in the apparatus body 100.

The ultrasound probe 11 is connected to the apparatus body 100 through a cable. In addition, the ultrasound probe 11 is brought into contact with a body surface of a subject P and transmits and receives ultrasound waves. For example, the ultrasound probe 11 includes a plurality of piezoelectric transducer elements (also referred to as transducer elements or ultrasound transducer elements) for transmitting and receiving ultrasound waves. These piezoelectric transducer elements generate ultrasound waves based on transmission signals supplied from the transmitter receiver circuitry 110. The generated ultrasound waves are reflected in body tissue in the subject P and are received by the piezoelectric transducer elements in the form of reflected wave signals. The ultrasound probe 11 transmits the reflected wave signals received by the piezoelectric transducer elements to the transmitter receiver circuitry 110.

The first embodiment can be applied to the ultrasound probe 11 whether the ultrasound probe 11 is a one-dimensional (1D) array probe that scans (two-dimensionally scans) a two-dimensional region inside the subject P or such a probe as a mechanical four-dimensional (4D) probe or a two-dimensional (2D) array probe that scans (three-dimensionally scans) a three-dimensional region inside the subject P.

The input device 12 corresponds to, for example, a mouse, a keyboard, a button, a panel switch, a touch command screen, a foot switch, a trackball, a joystick, or other devices. The input device 12 receives various setting requests from an operator of the ultrasound diagnosis apparatus 1 and forwards the received various setting requests to various circuits in the apparatus body 100 as appropriate.

The display 13 displays a graphical user interface (GUI) used by the operator for inputting various setting requests using the input device 12 and displays, for example, images (ultrasound images) based on ultrasound image data generated by the apparatus body 100.

The apparatus body 100 is an apparatus that generates ultrasound image data based on the reflected wave signals received by the ultrasound probe 11. As illustrated in FIG. 1, the apparatus body 100 includes, for example, the transmitter receiver circuitry 110, B-mode processing circuitry 120, Doppler processing circuitry 130, image generating circuitry 140, image memory 150, memory circuitry 160, and processing circuitry 170. The transmitter receiver circuitry 110, the B-mode processing circuitry 120, the Doppler processing circuitry 130, the image generating circuitry 140, the image memory 150, the memory circuitry 160, and the processing circuitry 170 are communicably connected to one another.

The transmitter receiver circuitry 110 controls transmission and reception of ultrasound waves by the ultrasound probe 11. For example, the transmitter receiver circuitry 110 includes transmitter circuitry 111 and receiver circuitry 112 and controls transmission and reception of ultrasound waves by the ultrasound probe 11, based on instructions from the processing circuitry 170 described later. The transmitter circuitry 111 generates transmission waveform data and generates, from the generated transmission waveform data, transmission signals that the ultrasound probe 11 uses for transmitting ultrasound waves. The transmitter circuitry 111 applies transmission signals to the ultrasound probe 11, thereby causing transmission of an ultrasound wave beam obtained by focusing ultrasound waves into a beam shape. The receiver circuitry 112 performs addition processing by assigning certain delay times to reflected wave signals received by the ultrasound probe 11, thereby generating reflected wave data in which reflection components from a direction agreeing with the reception directivity of the reflected wave signals are emphasized, and transmits the generated reflected wave data to the B-mode processing circuitry 120 and the Doppler processing circuitry 130.

The B-mode processing circuitry 120 applies various kinds of signal processing to the reflected wave data generated by the receiver circuitry 112 from the reflected wave signals. The B-mode processing circuitry 120 applies, for example, logarithmic amplification and envelope detection processing to the reflected wave data received from the receiver circuitry 112, thereby generating data (B-mode data) in which the signal intensity of each sample point (observation point) is expressed in brightness of luminance. The B-mode processing circuitry 120 transmits the generated B-mode data to the image generating circuitry 140.

In addition, the B-mode processing circuitry 120 performs signal processing for enabling harmonic imaging that visualizes harmonic components. Known examples of harmonic imaging include contrast harmonic imaging (CHI) and tissue harmonic imaging (THI). Known examples of a scanning method for CHI and THI include amplitude modulation and phase modulation.

The Doppler processing circuitry 130 generates, from the reflected wave data received by the receiver circuitry 112, data (Doppler data) into which pieces of motion information of a moving body based on the Doppler effect are extracted at respective sample points in a scanned region. Specifically, the Doppler processing circuitry 130 generates Doppler data into which average velocities, dispersion values, power values, or other values are extracted as the pieces of motion information of the moving body at the respective sample points. Examples of the moving body include a blood flow, tissue of a cardiac wall, and a contrast agent. The Doppler processing circuitry 130 transmits the generated Doppler data to the image generating circuitry 140.

The image generating circuitry 140 generates ultrasound image data from the data generated by the B-mode processing circuitry 120 and the Doppler processing circuitry 130. For example, the image generating circuitry 140 generates, from the B-mode data generated by the B-mode processing circuitry 120, B-mode image data in which the intensity of a reflected wave is expressed in luminance. The image generating circuitry 140 also generates Doppler image data representing moving body information from the Doppler data generated by the Doppler processing circuitry 130. The Doppler image data is speed image data, dispersion image data, power image data, or image data obtained by combining any of the foregoing data.

The image memory 150 is a memory that stores therein data generated by the B-mode processing circuitry 120, the Doppler processing circuitry 130, and the image generating circuitry 140. For example, the image memory 150 stores therein the ultrasound image data generated by the image generating circuitry 140, in association with electrocardiographic waveforms of the subject P. When the amount of data to be stored in the image memory 150 exceeds the memory capacity of the image memory 150, relatively old data is deleted and updated.

The memory circuitry 160 is a storage device that stores therein various kinds of data. For example, the memory circuitry 160 stores therein: control programs for performing transmission and reception of ultrasound waves, image processing, and display processing; diagnosis information (for example, patient IDs and doctor's opinions); and various kinds of data such as diagnosis protocols and various body marks. Data stored in the memory circuitry 160 can be transferred to an external device via an interface (not illustrated).

In addition, the memory circuitry 160 stores therein data generated by the B-mode processing circuitry 120, the Doppler processing circuitry 130, and the image generating circuitry 140. For example, the memory circuitry 160 stores therein ultrasound image data corresponding to a certain number of heartbeats as specified by the operator. The memory circuitry 160 is one example of storage circuitry that stores therein a plurality of images acquired by scanning the subject P for a certain time period.

The processing circuitry 170 controls all processing in the ultrasound diagnosis apparatus 1. Specifically, based on various setting requests input from the operator via the input device 12 and various control programs and various data loaded from the memory circuitry 160, the processing circuitry 170 controls processing in the transmitter receiver circuitry 110, the B-mode processing circuitry 120, the Doppler processing circuitry 130, and the image generating circuitry 140. The processing circuitry 170 causes the display 13 to display ultrasound image data stored in the image memory 150.

Furthermore, a plurality of components in FIG. 1 may be integrated into one processor to implement the functions thereof. The term "processor" used in the foregoing descriptions means, for example, a central processing unit (CPU), a graphics processing unit (GPU), or a circuit such as an application specific integrated circuit (ASIC) or a programmable logic device (examples of which include a simple programmable logic device (SPLD), a complex programmable logic device (CPLD), and a field programmable gate array (FPGA)). The processor reads out a computer program stored in memory circuitry and executes the computer program to implement a function. Instead of being stored in the memory circuitry 160, the computer program may be configured to be embedded directly in a circuit of the processor. In this case, the processor reads out the computer program embedded in the circuitry and executes the computer program to implement the function. Each processor of this embodiment is not limited to a processor configured as a single circuit, and may be configured as a single processor having a plurality of independent circuits combined therein to implement an intended function.

Figure 2:
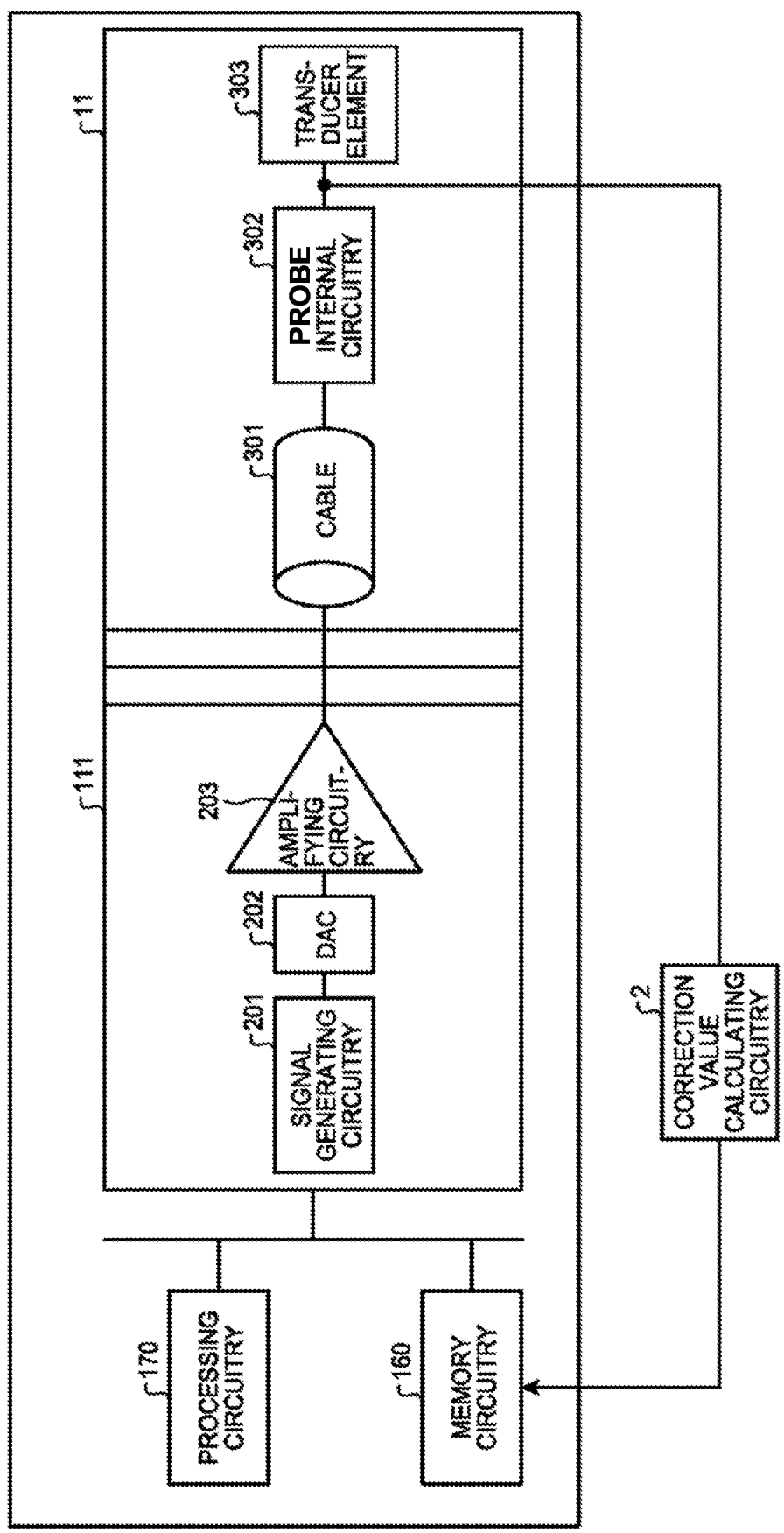
FIG. 2 is a diagram for explaining the first embodiment.

The ultrasound diagnosis apparatus 1 configured as above may perform, for example, harmonic imaging by a method in which a plurality of ultrasound waves with different phases are transmitted successively to visualize harmonic components. With reference to FIG. 2, the following describes transfer of transmission signals between the transmitter circuitry 111 and the ultrasound probe 11 in the case of performing harmonic imaging by the method in which a plurality of ultrasound waves with different phases are transmitted successively to visualize harmonic components. FIG. 2 is a diagram for explaining the first embodiment. For the convenience of description, FIG. 2 illustrates the ultrasound probe 11, the transmitter circuitry 111, the memory circuitry 160, and the processing circuitry 170 among the components included in the ultrasound diagnosis apparatus 1. As illustrated in FIG. 2, correction value calculating circuitry 2 is connected to the ultrasound diagnosis apparatus 1.

As illustrated in FIG. 2, the transmitter circuitry 111 includes signal generating circuitry 201, a digital-analog converter (DAC) 202, and amplifying circuitry 203. The transmitter circuitry 111 generates transmission waveform data, generates, from the generated transmission waveform data, transmission signals that the ultrasound probe 11 uses for transmitting ultrasound waves, and outputs the generated transmission signals to the ultrasound probe 11.

The signal generating circuitry 201 generates the transmission waveform data, and outputs the generated transmission waveform data to the DAC 202. The following exemplifies a case in which the ultrasound probe 11 transmits an ultrasound wave with a phase of 0 degrees and an ultrasound wave with a phase of 180 degrees. In this case, the signal generating circuitry 201 generates transmission waveform data of the ultrasound wave with a phase of 0 degrees (0 deg transmission waveform data) and transmission waveform data of the ultrasound wave with a phase of 180 degrees (180 deg transmission waveform data). That is, the signal generating circuitry 201 generates a plurality of pieces of transmission waveform data that causes a sum component to be zero. The signal generating circuitry 201 outputs the generated 0 deg transmission waveform data and 180 deg transmission waveform data to the DAC 202.

The DAC 202 converts the transmission waveform data to analog signals, and outputs the converted analog signals of the transmission waveform data to the amplifying circuitry 203. The amplifying circuitry 203 amplifies the analog signals of the transmission waveform data to generate transmission signals, and outputs the generated transmission signals to the ultrasound probe 11.

As illustrated in FIG. 2, the ultrasound probe 11 includes a cable 301, probe internal circuitry 302, and a transducer element 303. The cable 301 outputs the transmission signals generated by the transmitter circuitry 111 to the probe internal circuitry 302. The probe internal circuitry 302 includes a semiconductor switch for switching the cable 301, a semiconductor switch for switching the transducer element 303, and serial or parallel tuning circuitry including an inductor or other elements. The transducer element 303 transmits and receives ultrasound waves based on the transmission signals generated from the transmission waveform data by the apparatus body 100 of the ultrasound diagnosis apparatus 1.

In some cases, although the transmitter circuitry 111 has generated a plurality of pieces of transmission waveform data that causes a sum component to be zero, the sum component of transmission signals applied to the ultrasound probe 11 or the sum component of ultrasound waves transmitted from the ultrasound probe 11 may not completely be canceled out and may leave a residual component.

Specifically, the amplifying circuitry 203 of the transmitter circuitry 111 generates a transmission signal with positive phase polarity and a transmission signal with negative phase polarity by a p-type semiconductor using holes as carriers and a n-type semiconductor using electrons as carriers. In this configuration, ensuring the symmetry of the phase polarities of transmission signals may be difficult. In addition, the impedance of the transducer element 303 changes between positive amplitude and negative amplitude of transmission signals. This change causes asymmetry of phase polarities. The degree of asymmetry of the phase polarities in the transducer element 303 increases at larger amplitude.

A residual component of the transmission signals left in the frequency band of a harmonic component generates a problem of degraded signal to noise (S/N) ratio. Specifically, reflected wave signals obtained by transmitting ultrasound waves based on two transmission signals include a harmonic component generated from nonlinearity of a living body intended to be imaged, and a reflected wave signal for the residual component of the transmission signals. The reflected wave signal for the residual component of the transmission signals is not canceled out and imaged as noise.

Thus, when causing the ultrasound probe 11 to transmit a plurality of ultrasound waves with different phases successively depending on a transmission condition, the transmitter circuitry 111 of the ultrasound diagnosis apparatus 1 according to the first embodiment generates transmission waveform data based on which a sum component of the ultrasound waves transmitted successively is within a certain range, by using transmission signals detected between the cable and the ultrasound transducer element. For example, the transmitter circuitry 111 generates transmission waveform data based on a plurality of pieces of uncorrected transmission waveform data corresponding to a plurality of respective ultrasound waves transmitted successively depending on a transmission condition and causing a sum component to be zero, and a correction value dependent on the transmission condition.

The memory circuitry 160, for example, stores therein the correction value dependent on the transmission condition. For example, the correction value is set depending on a mode such as THI, CHI, or phase modulation. When receiving a mode selected by the operator via the GUI displayed on the display 13, for example, the transmitter circuitry 111 reads out the correction value of the selected mode and generates transmission waveform data. The correction value may be set in association with transmission voltage and transmission frequency. In this case, for example, when receiving a transmission voltage and a transmission frequency selected by the operator via the GUI displayed on the display 13, the transmitter circuitry 111 reads out the associated correction value and generates transmission waveform data.

The following describes calculation processing of the correction value. The first embodiment describes a case in which the correction value is calculated, for example, by an apparatus other than the ultrasound diagnosis apparatus 1 before shipment of the ultrasound diagnosis apparatus 1. In this case, it is assumed that the correction value calculating circuitry 2 calculates the correction value. Calculation processing of the correction value is preferably performed by bringing the ultrasound probe 11 into contact with a subject having acoustic impedance similar to that of a living body, such as water or a phantom. The correction value calculating circuitry 2 is an example calculation circuitry.

The transmitter circuitry 111 generates a plurality of pieces of uncorrected transmission waveform data corresponding to a plurality of respective ultrasound waves transmitted successively depending on a transmission condition and causing a sum component to be zero, and then generates a plurality of uncorrected transmission signals corresponding to the respective generated pieces of uncorrected transmission waveform data. For example, the transmission signals generated from the uncorrected transmission waveform data generated by the signal generating circuitry 201 deform due to noise or other factors mixed in before the transmission signals are applied to the transducer element 303. That is, a transmission signal obtained by logical conversion of the uncorrected transmission waveform data generated by the signal generating circuitry 201 from which mixed noise or other factors are removed differs from an actual transmission signal applied to the transducer element 303.

Specifically, noise or other factors are mixed in the logically converted transmission signal while the transmission signal is processed by the DAC 202, the amplifying circuitry 203, or other circuits, and passing through the probe internal circuitry 302 of the ultrasound probe 11. A logical transmission signal with a phase of 0 degrees is denoted as Sin p and a logical transmission signal with a phase of 180 degrees is denoted as Sin n when the uncorrected transmission waveform data generated by the signal generating circuitry 201 is assumed to be converted to logical transmission signals from which noise or other factors are removed.

The correction value calculating circuitry 2 acquires, as an uncorrected sum component, a sum component of the uncorrected transmission signals acquired at a point in time from immediately after generation of the signals to immediately before application of the signals to the transducer element 303 in the ultrasound probe 11, or a sum component of the uncorrected ultrasound waves each acquired at the point when the ultrasound probe 11 transmits the ultrasound waves based on the respective uncorrected transmission signals. For example, the correction value calculating circuitry 2 acquires the plurality of the uncorrected transmission signals from the probe internal circuitry 302 and acquires the sum component of the uncorrected transmission signals by adding the plurality of the uncorrected transmission signals. The sum component of the uncorrected transmission signals is represented as a time-base waveform $\Delta So(t)$ by "Sop(t)+Son(t)", where Sop is the acquired uncorrected transmission signal with a phase of 0 degrees and Son is the acquired uncorrected transmission signal with a phase of 180 degrees. The correction value calculating circuitry 2 calculates a correction value based on the acquired uncorrected sum component. That is, $\Delta So(t)$ is a residual component of the transmission waveforms that has not been canceled. The correction value of the transmission waveform data is calculated such that $\Delta So(t)$ is within a certain range. The following describes a case of calculating a correction value that provides a minimum $\Delta So(t)$.

For example, the correction value calculating circuitry 2 applies fast Fourier transform (FFT) to $\Delta So(t)$ to convert $\Delta So(t)$ to a frequency spectrum $\Delta So(\omega)$. On the frequency axis, the correction value calculating circuitry 2 multiplies $\Delta So(\omega)$ by a frequency window function that weights a frequency band that needs to be canceled. For example, the correction value calculating circuitry 2 multiplies a frequency band of a nonlinear component of a living body, the frequency band being around second harmonic components, by the frequency window function. That is, the correction value calculating circuitry 2 derives a frequency spectrum by weighting a certain frequency band corresponding to the transmission condition in the frequency spectrum of the uncorrected sum component.

Subsequently, the correction value calculating circuitry 2 calculates a conversion component from a conversion spectrum calculated from a conversion function and the frequency spectrum obtained by weighting a certain frequency band corresponding to the transmission condition in the frequency spectrum of the uncorrected sum component. The conversion function is a function that corrects a waveform by considering noise so as to convert the waveform back to that of the transmission waveform data that has been used to generate the waveform, the waveform acquired at a point in time from immediately after generation of signals to immediately before application of the signals to the transducer element 303 in the ultrasound probe 11, or at the point when the ultrasound probe 11 transmits the waveform based on corresponding one of the uncorrected transmission signals. In other words, the conversion function converts a frequency spectrum of a waveform acquired at a point in time from immediately after generation of signals to immediately before application of the signals to the transducer element 303 in the ultrasound probe 11, or a frequency spectrum of a waveform acquired at the point when the ultrasound probe 11 transmits the waveform based on corresponding one of the uncorrected transmission signals, back to the frequency spectrum of a waveform of the transmission waveform data that has been used to generate the waveform at the point in time.

The conversion function for the uncorrected transmission signal with a phase of 0 degrees, Sop, is denoted as $Hinvp(\omega)$, and the conversion function for the uncorrected transmission signal with a phase of 180 degrees, Son, is denoted as $Hinvn(\omega)$. A conversion function is set for each transmission condition. For example, the conversion function is determined depending on a transmission voltage and a transmission frequency in a transmission condition. The conversion function may be set for each mode. For example, the conversion function for CHI or the conversion function for THI may be set.

For example, the correction value calculating circuitry 2 calculates a correction value based on the conversion component obtained by converting the uncorrected sum component by a conversion function. Specifically, the correction value calculating circuitry 2 derives $\Delta \sin(\omega)$ by multiplying $\Delta So(\omega)$, which has been multiplied by the frequency window function, by the conversion function $Hinvp(\omega)$ or $Hinvn(\omega)$. The correction value calculating circuitry 2 may determine that halves of $\Delta So(t)$ are a nonlinear component of Sop(t) and a nonlinear component of Son(t), respectively, and multiply Sop(t) by the conversion function $Hinvp(\omega)$ and Son(t) by the conversion function $Hinvn(\omega)$. Alternatively, the correction value calculating circuitry 2 may determine $\Delta So(t)$ to be the nonlinear component of Sop(t) and multiply Sop(t) by the conversion function $Hinvp(\omega)$, or determine $\Delta So(t)$ to be the nonlinear component of Son(t) and multiply Son(t) by the conversion function $Hinvn(\omega)$.

The correction value calculating circuitry 2 applies inverse FFT to the conversion component $\Delta \sin(\omega)$ to convert $\Delta \sin(\omega)$ back to time-based representation, thereby deriving the correction value. The correction value calculating circuitry 2 stores the derived correction value in the memory circuitry 160. The transmitter circuitry 111 generates transmission waveform data by, for example, subtracting the correction value from the uncorrected transmission waveform data. The correction value calculating circuitry 2 may repeat the same correction processing on the results of ultrasound waves transmitted based on the corrected transmission waveform data. For example, the correction value calculating circuitry 2 may repeat the correction processing a certain number of times or until ΔSo reaches a certain value or smaller.

Figure 3:
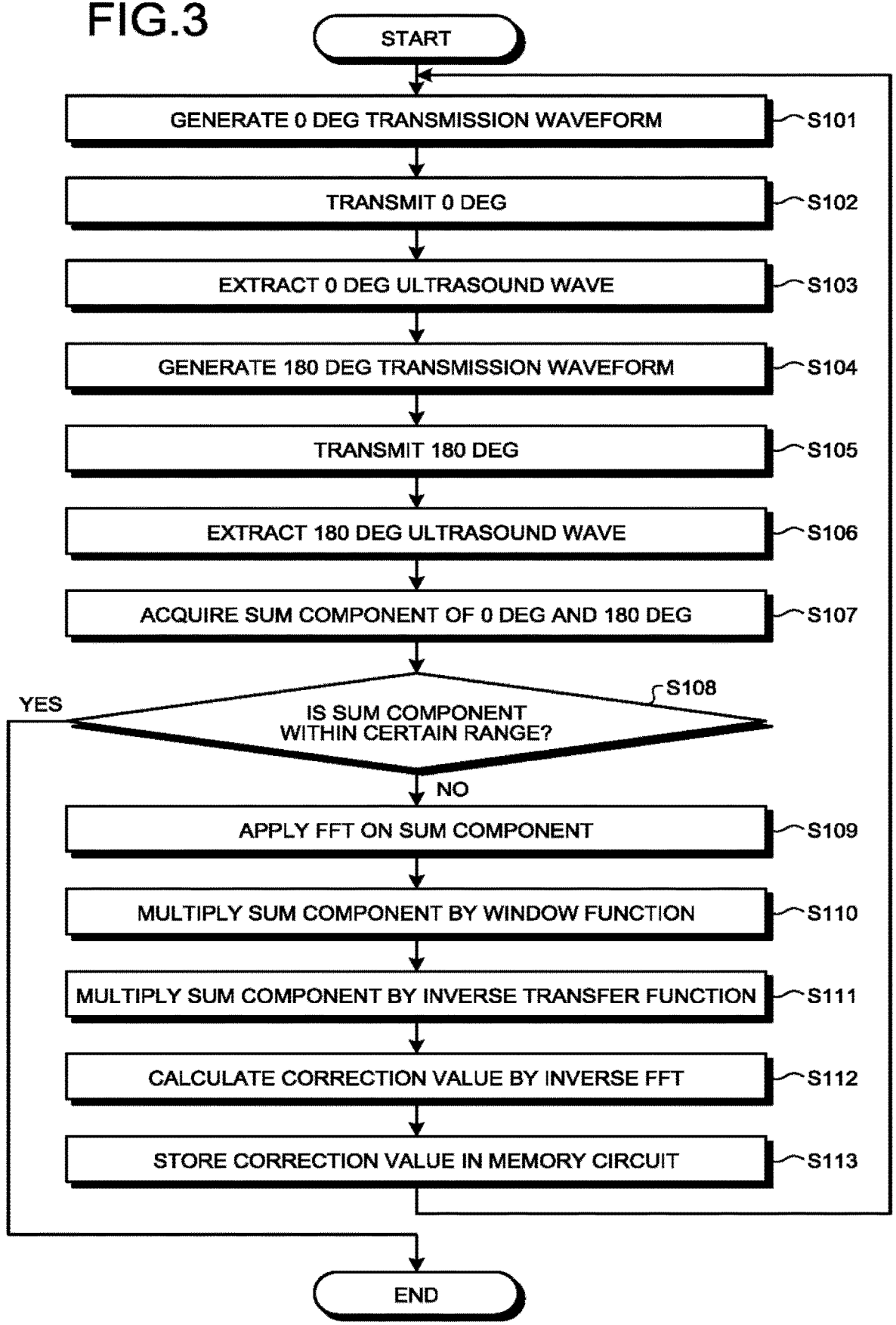
FIG. 3 is a flowchart illustrating a procedure of calculating a correction value according to the first embodiment.

FIG. 3 is a flowchart illustrating a procedure of calculating a correction value according to the first embodiment. The transmitter circuitry 111 generates 0 deg transmission waveform data (Step S101), and causes the ultrasound probe 11 to transmit the generated 0 deg transmission waveform data (Step S102). Subsequently, the correction value calculating circuitry 2 extracts a 0 deg ultrasound wave (Step S103).

The transmitter circuitry 111 generates 180 deg transmission waveform data (Step S104), and causes the ultrasound probe 11 to transmit the generated 180 deg transmission waveform data (Step S105). Subsequently, the correction value calculating circuitry 2 extracts a 180 deg ultrasound wave (Step S106). The correction value calculating circuitry 2 acquires a sum component of the 0 deg ultrasound wave and the 180 deg ultrasound wave (Step S107).

The correction value calculating circuitry 2 determines whether the sum component is within a certain range (Step S108). If the correction value calculating circuitry 2 determines that the sum component is within the certain range (Yes at Step S108), the process ends. If the correction value calculating circuitry 2 does not determine that the sum component is within the certain range (No at Step S108), FFT is applied to the sum component (Step S109).

Subsequently, the correction value calculating circuitry 2 multiplies the sum component by a window function (Step S110), and then by an inverse transfer function (Step S11). The correction value calculating circuitry 2 applies inverse FFT to calculate a correction value (Step S112). The correction value calculating circuitry 2 stores the correction value in the memory circuitry 160 (Step S113). After Step S113 is completed, the process proceeds to Step S101.

As described above, when causing the ultrasound probe 11 to transmit a plurality of ultrasound waves with different phases successively depending on a transmission condition, the ultrasound diagnosis apparatus 1 according to the first embodiment generates transmission waveform data based on which a sum component of the ultrasound waves transmitted successively is within a certain range. Thus, the ultrasound diagnosis apparatus 1 according to the first embodiment can reduce noise in an image of a harmonic component generated by transmitting a plurality of ultrasound waves with different phases. Specifically, a nonlinear component from a living body is imaged with reduced degradation of S/N ratio, the degradation being caused by an uncanceled residual component generated by the nonlinearity of the uncorrected transmission signals. The sum component of the uncorrected transmission signals tends to be strongly affected by the amplifying circuitry 203 when transmission voltage is small, and more strongly affected by the transducer element 303 when the transmission voltage becomes larger. Thus, the ultrasound diagnosis apparatus 1 according to the first embodiment can also perform correction with the properties of the transducer element 303 being considered.

The ultrasound diagnosis apparatus 1 according to the first embodiment generates transmission waveform data based on which a sum component of the ultrasound waves transmitted successively is within a certain range, by using transmission signals detected between the cable 301 and the transducer element 303. This configuration enables generation of transmission waveform data that is not affected by the impedance of the cable 301.

Specifically, when transmission waveform data is generated by using transmission signals detected between the amplifying circuitry 203 and the cable 301, the phase polarities of transmission signals immediately before input to the cable 301 are symmetric. However, the transmission signals after passing through the cable 301 have been affected by the impedance of the cable 301, and thus the phase polarities of the transmission signals are asymmetric. Thus, using the transmission signals detected between the amplifying circuitry 203 and the cable 301 to generate transmission waveform data based on which a sum component of the ultrasound waves transmitted successively is within a certain range does not provide transmission signals with symmetric phase polarities at the transducer element 303. In contrast, the ultrasound diagnosis apparatus 1 according to the first embodiment generates transmission waveform data based on which a sum component of the ultrasound waves transmitted successively is within a certain range, by using transmission signals detected between the cable 301 and the transducer element 303. That is, the ultrasound diagnosis apparatus 1 according to the first embodiment generates transmission waveform data by considering the effect of the impedance of the cable 301. Consequently, the ultrasound diagnosis apparatus 1 according to the first embodiment provides transmission signals having symmetric phase polarities at the transducer element 303.

Examples of harmonic imaging include CHI and THI. CHI transmits ultrasound waves at small amplitude to capture nonlinear behavior of contrast agent bubbles without breaking the bubbles. THI transmits ultrasound waves at large amplitude to generate the actual nonlinearity of a living body. Thus, the transmitter circuitry 111 needs to maintain the symmetry of positive and negative polarities when the phases are inverted under both conditions of CHI and THI. In the first embodiment described above, when causing the ultrasound probe 11 to transmit a plurality of ultrasound waves with different phases successively depending on a transmission condition, the ultrasound diagnosis apparatus 1 generates transmission waveform data based on which a sum component of the ultrasound waves transmitted successively is within a certain range. As a result, the ultrasound diagnosis apparatus 1 according to the first embodiment can maintain the symmetry of positive and negative polarities when the phases are inverted in both CHI transmitting ultrasound waves at small amplitude and THI transmitting ultrasound waves at large amplitude. Thus, the ultrasound diagnosis apparatus 1 according to the first embodiment can perform correction to improve S/N ratio of both the transmission at small amplitude to image the nonlinearity of a contrast agent and the transmission at large amplitude to image the actual nonlinearity of a living body.

In the above embodiment, the case is described where the correction value calculating circuitry 2 acquires, as an uncorrected sum component, a sum component of a plurality of uncorrected transmission signals acquired at a point in time from immediately after generation of the signals to immediately before application of the signals to the transducer element 303 in the ultrasound probe 11. However, the embodiment is not limited to this case. For example, the correction value calculating circuitry 2 may acquire, as an uncorrected sum component, a sum component of a plurality of uncorrected ultrasound waves each acquired at the point in time when the ultrasound probe 11 transmits the ultrasound waves based on the respective uncorrected transmission signals. In this case, the correction value calculating circuitry 2 acquires a plurality of uncorrected ultrasound waves measured by a hydrophone and acquires a sum component of the uncorrected ultrasound waves by adding the plurality of the uncorrected ultrasound waves, for example.

Second Embodiment

In the first embodiment, a case has been described in which the correction value is calculated by an external apparatus other than the ultrasound diagnosis apparatus 1, for example, before shipment, and stored in the memory circuitry 160. The second embodiment describes a case in which the correction value is calculated by an ultrasound diagnosis apparatus.

Figure 4:
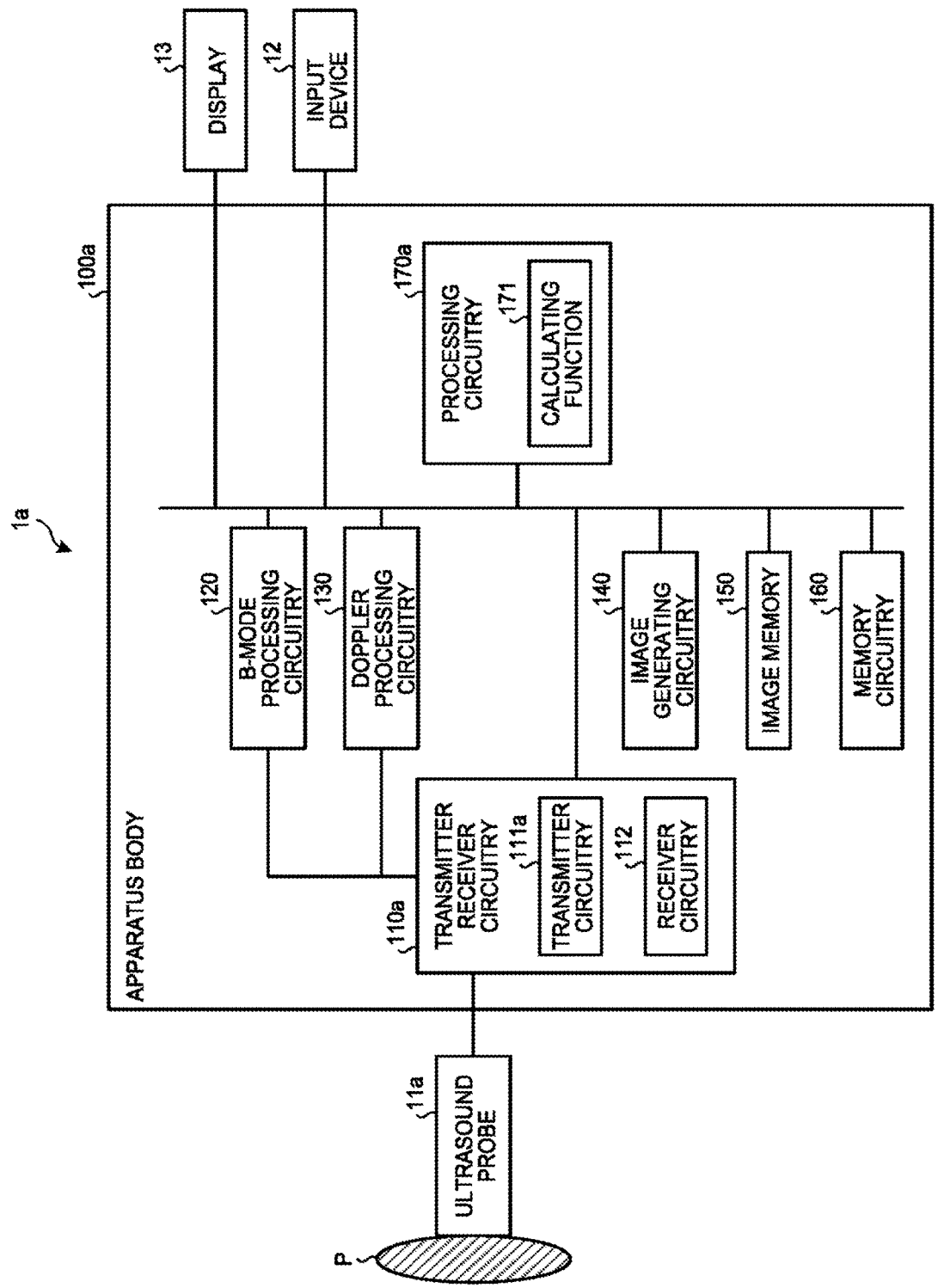
FIG. 4 is a block diagram illustrating an exemplary configuration of an ultrasound diagnosis apparatus according to a second embodiment.

FIG. 4 is a block diagram illustrating an exemplary configuration of an ultrasound diagnosis apparatus 1a according to the second embodiment. As illustrated in FIG. 4, the ultrasound diagnosis apparatus 1a according to the second embodiment includes an ultrasound probe 11a, the input device 12, the display 13, and an apparatus body 100a. Among the components included in the ultrasound diagnosis apparatus 1a illustrated in FIG. 4, the components having the same functions as those of the components illustrated in FIG. 1 are assigned with the same reference signs and detailed descriptions thereof are omitted. Furthermore, similarly to the case of FIG. 1, a plurality of components in FIG. 4 may be integrated into one processor to implement the functions thereof.

The apparatus body 100a is an apparatus that generates ultrasound image data based on the reflected wave signals received by the ultrasound probe 11a. The configuration of the apparatus body 100a is the same as the configuration of the apparatus body 100 according to the first embodiment except that the configuration of transmitter receiver circuitry 110a and processing circuitry 170a is different. As illustrated in FIG. 4, the apparatus body 100a includes, for example, the transmitter receiver circuitry 110a, the B-mode processing circuitry 120, the Doppler processing circuitry 130, the image generating circuitry 140, the image memory 150, the memory circuitry 160, and the processing circuitry 170a. Among the components included in the apparatus body 100a illustrated in FIG. 4, the components having the same functions as those of the components illustrated in FIG. 1 are assigned with the same reference signs and detailed descriptions thereof are omitted.

The transmitter receiver circuitry 110a controls transmission and reception of ultrasound waves by the ultrasound probe 11a. For example, the transmitter receiver circuitry 110a includes transmitter circuitry 111a and the receiver circuitry 112 and controls transmission and reception of ultrasound waves by the ultrasound probe 11a, based on instructions from the processing circuitry 170a described later. The configuration of the transmitter receiver circuitry 110a according to the second embodiment is the same as the configuration of the transmitter receiver circuitry 110 according to the first embodiment except that the configuration of a part of the transmitter circuitry 111a is different. In the same manner as the transmitter circuitry 111 according to the first embodiment performs, the transmitter circuitry 111a according to the second embodiment generates transmission waveform data, generates, from the generated transmission waveform data, transmission signals that the ultrasound probe 11a uses for transmitting ultrasound waves, and outputs the generated transmission signals to the ultrasound probe 11a. For example, the transmitter circuitry 111a generates transmission waveform data based on a plurality of pieces of uncorrected transmission waveform data corresponding to a plurality of respective ultrasound waves transmitted successively depending on a transmission condition and causing a sum component to be zero, and a correction value dependent on the transmission condition.

The processing circuitry 170a controls all processing in the ultrasound diagnosis apparatus 1a. The configuration of the processing circuitry 170a according to the second embodiment is the same as the configuration of the processing circuitry 170 according to the first embodiment except that the processing circuitry 170a includes a calculating function 171. The calculating function 171 is a function that is implemented by the processing circuitry 170a reading out and executing a computer program corresponding to the calculating function 171 from the memory circuitry 160. The calculating function 171 is an example calculation circuitry. In FIG. 4, it is described that the single processing circuitry 170a implements the processing function performed by the calculating function 171. However, a plurality of independent processors may be combined to be processing circuitry and each of the processors may execute a computer program, thereby implementing the function.

Figure 5:
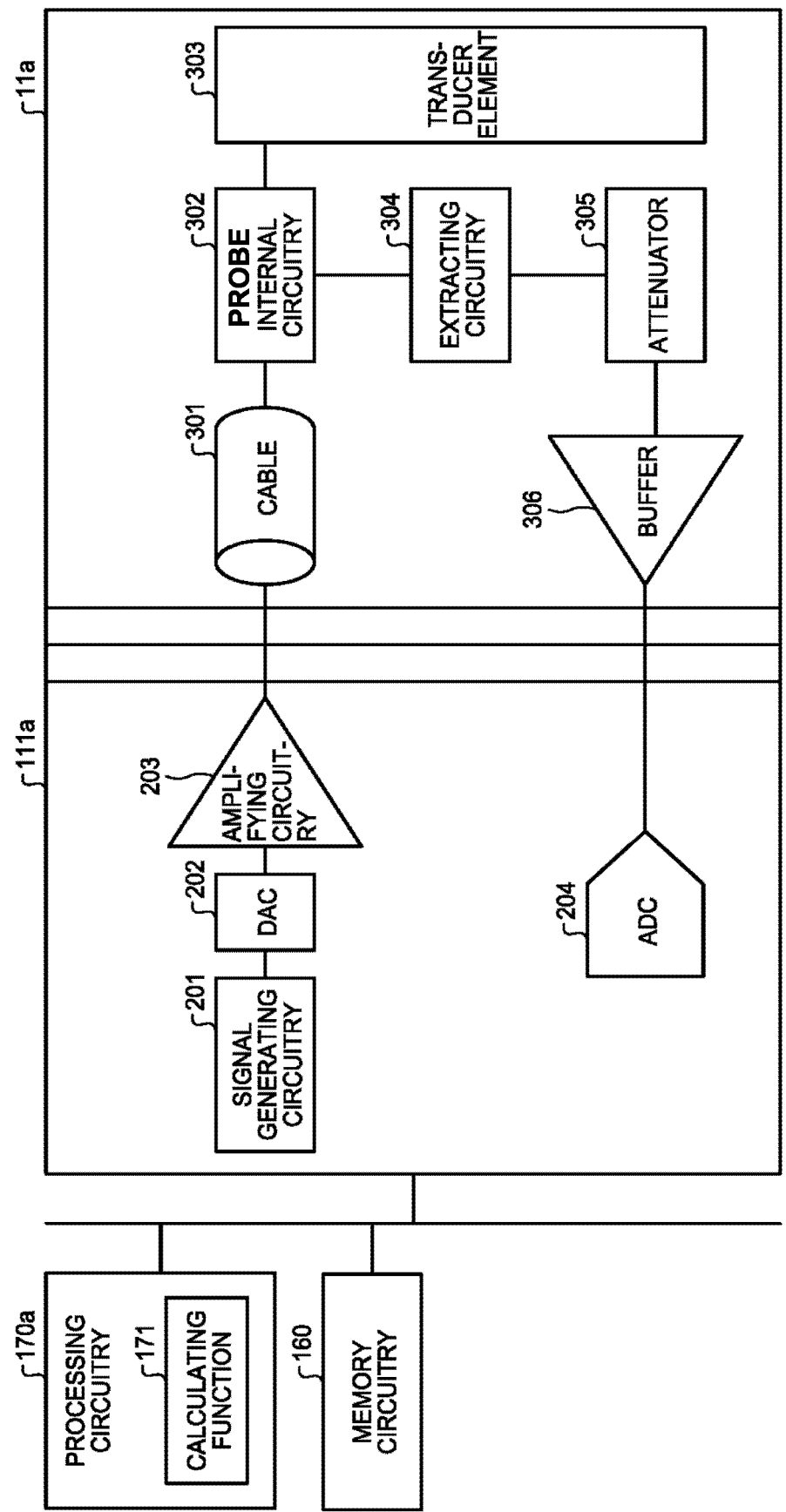
FIG. 5 is a diagram for explaining the second embodiment.

The following describes the ultrasound probe 11a, the transmitter circuitry 11a, and the processing circuitry 170a with reference to FIG. 5. FIG. 5 is a diagram for explaining the second embodiment. For the convenience of description, FIG. 5 illustrates the ultrasound probe 11a, the transmitter circuitry 111a, the memory circuitry 160, and the processing circuitry 170a among the components included in the ultrasound diagnosis apparatus 1a.

The ultrasound probe 11a is communicably connected to the transmitter receiver circuitry 110a described later, which is included in the apparatus body 100a. The ultrasound probe 11a further includes extracting circuitry 304 that outputs the plurality of the uncorrected transmission signals to the calculating function. For example, as illustrated in FIG. 5, the ultrasound probe 11a includes the cable 301, the probe internal circuitry 302, the transducer element 303, the extracting circuitry 304, an attenuator 305, and a buffer 306. Among the components included in the ultrasound probe 11a, the components having the same functions as those of the components of the ultrasound probe 11 according to the first embodiment are assigned with the same reference signs and detailed descriptions thereof are omitted.

The extracting circuitry 304 acquires the plurality of the uncorrected transmission signals from the probe internal circuitry 302 and outputs the plurality of the uncorrected transmission signals to the calculating function 171 via the attenuator 305. The attenuator 305 attenuates the uncorrected transmission signals extracted by the extracting circuitry 304 when the plurality of the uncorrected transmission signals cannot directly be stored in the buffer 306 due to large amplitude. The buffer 306 outputs the uncorrected transmission signals output by the attenuator 305 to an analog-digital converter (ADC) 204.

As illustrated in FIG. 5, the transmitter circuitry 111a includes the signal generating circuitry 201, the DAC 202, the amplifying circuitry 203, and the ADC 204. Among the components included in the transmitter circuitry 111a, the components having the same functions as those of the components of the transmitter circuitry 111 according to the first embodiment are assigned with the same reference signs and detailed descriptions thereof are omitted.

The ADC 204 digitally converts the uncorrected transmission signals output from the buffer 306 and outputs the converted component to the calculating function 171.

The calculating function 171 has the same function as the correction value calculating circuitry 2 according to the first embodiment. That is, the calculating function 171 acquires, as an uncorrected sum component, a sum component of a plurality of uncorrected transmission signals acquired at a point in time from immediately after generation of the signals to immediately before application of the signals to the transducer element 303 in the ultrasound probe 11a, or a sum component of a plurality of uncorrected ultrasound waves each acquired at the point when the ultrasound probe 11a transmits the ultrasound waves based on the respective uncorrected transmission signals. For example, the calculating function 171 acquires the plurality of the uncorrected transmission signals output by the extracting circuitry 304 and acquires the sum component of the uncorrected transmission signals by adding the plurality of the uncorrected transmission signals. Alternatively, for example, the calculating function 171 acquires a plurality of uncorrected ultrasound waves measured by a hydrophone and acquires a sum component of the uncorrected ultrasound waves by adding the plurality of the uncorrected ultrasound waves. The calculating function 171 calculates a correction value based on the acquired uncorrected sum component.

When the calculating function 171 acquires the plurality of the uncorrected transmission signals, the plurality of the uncorrected transmission signals passes through the extracting circuitry 304, the attenuator 305, the buffer 306, and the ADC 204. The extracting circuitry 304, the attenuator 305, the buffer 306, and the ADC 204 are also collectively referred to as correcting circuitry. The plurality of the uncorrected transmission signals acquired by the calculating function 171 may contain noise mixed in the course of passing through the correcting circuitry. Thus, the calculating function 171 multiplies the acquired sum component of the uncorrected transmission signals by a conversion function for the correcting circuitry to derive a sum component $\Delta So(t)$ of the uncorrected transmission signals from which the effect of noise mixed in the course of passing through the correcting circuitry is removed. The conversion function for the correcting circuitry is a function that corrects the sum component by considering noise so as to convert the sum component back to the sum component of the uncorrected transmission signals at the point in time when being output from the probe internal circuitry 302, the sum component of the uncorrected transmission signals acquired by the calculating function 171.

After deriving $\Delta So(t)$, the calculating function 171 calculates a correction value in the same manner as the correction value calculating circuitry 2 according to the first embodiment performs.

Deriving in advance a transfer function for the correcting circuitry, the conversion function $Hinvp(\omega)$, and the conversion function $Hinvn(\omega)$ described in the first embodiment enables acquisition of the plurality of the uncorrected transmission signals, calculation of a correction value, and correction by subtraction in the ultrasound diagnosis apparatus 1a. This configuration facilitates acquisition of a correction value depending on a transmission condition, such as the number of waves, frequency, and voltage, or for each ultrasound probe 11a. Thus, the ultrasound diagnosis apparatus 1a according to the second embodiment can calculate a correction value in real time when the correction value has not been calculated, so as to generate transmission waveform data based on which a sum component of a plurality of ultrasound waves transmitted successively is within a certain range. This configuration also enables calculation of an appropriate correction value every time modes are switched. Consequently, transmission waveform data based on which a sum component of a plurality of ultrasound waves transmitted successively is within a certain range can be generated every time modes are switched.

When the ultrasound probe 11a alone is newly purchased, an appropriate correction value can be calculated by simply deriving the transfer function for the correcting circuitry, the conversion function $Hinvp(\omega)$, and the conversion function $Hinvn(\omega)$ between the ultrasound probe 11a and the existing apparatus body 100a. Consequently, transmission waveform data based on which a sum component of a plurality of ultrasound waves transmitted successively is within a certain range can be generated.

The correcting circuitry does not need to be provided to every transducer element. That is, the correcting circuitry may be provided for at least one representative channel of uncorrected transmission signals. In other words, the extracting circuitry 304 may extract a plurality of uncorrected transmission signals output to a certain transducer element among a plurality of transducer elements 303 in the ultrasound probe 11a. When the extracting circuitry 304, the attenuator 305, and the buffer 306 are implemented in the ultrasound probe 11a, the number of circuits is preferably limited to the smallest necessary number in order to prevent the temperature the probe from being increased by power consumption.

The calculating function 171 may report an abnormality when the calculated correction value is outside the certain range. For example, a settable range for a correction value is specified in advance to prevent an acoustic power limit from being exceeded by an abnormal value. If a correction value is outside this range, the calculating function 171 determines the value as abnormal, reports an error, and stops transmitting ultrasound waves. Because a correction value is typically equal to or smaller than 3% of amplitude, which is a small value, the acoustic power limit will not be exceeded if a default value of the acoustic power is set to a lower value in advance with the correction value being considered. Thus, the effect on sensitivity is significantly small, which causes no problem.

Similarly to the ultrasound diagnosis apparatus 1 according to the first embodiment, the ultrasound diagnosis apparatus 1a according to the second embodiment generates transmission waveform data based on which a sum component of a plurality of ultrasound waves transmitted successively is within a certain range, by using transmission signals detected between the cable 301 and the transducer element 303. This configuration enables generation of transmission waveform data that is not affected by the impedance of the cable 301. Consequently, the ultrasound diagnosis apparatus 1a according to the second embodiment provides transmission signals having symmetric phase polarities at the transducer element 303.

Modification of Second Embodiment

In the second embodiment, the case is described where a plurality of uncorrected transmission signals is extracted from the ultrasound probe 11a. However, the embodiment is not limited to this case. For example, if a dominant factor causing a residue is the amplifying circuitry 203 and thus the effect of noise mixed due to the ultrasound probe 11a does not need to be considered, the plurality of the uncorrected transmission signals may be extracted from, for example, an output from the amplifying circuitry 203 in the transmitter circuitry 11a.

Figure 6:
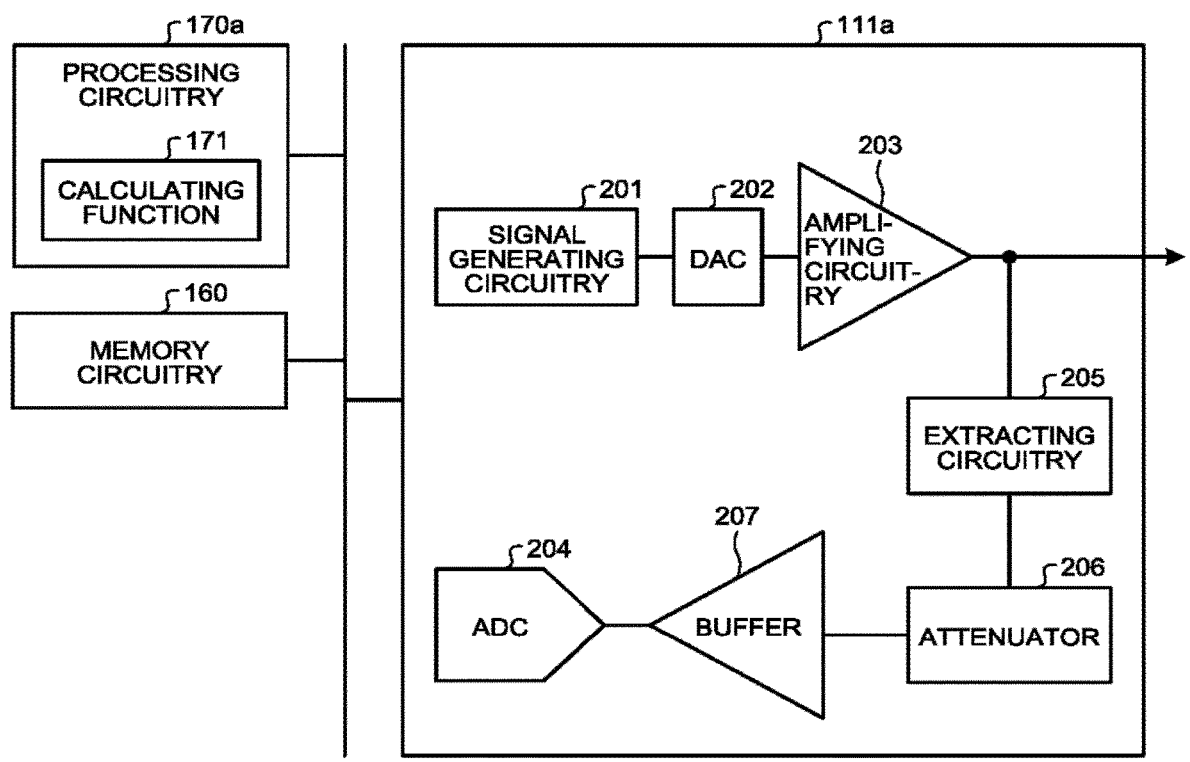
FIG. 6 is a diagram for explaining a modification of the second embodiment.

FIG. 6 is a diagram for explaining a modification of the second embodiment. The transmitter circuitry 111a according to the modification of the second embodiment includes the signal generating circuitry 201, the DAC 202, the amplifying circuitry 203, the ADC 204, extracting circuitry 205, an attenuator 206, and a buffer 207. Among the components included in the transmitter circuitry 111a according to the modification of the second embodiment, the components having the same functions as those of the components of the transmitter circuitry 111a according to the second embodiment are assigned with the same reference signs and detailed descriptions thereof are omitted.

The extracting circuitry 205 outputs a plurality of uncorrected transmission signals output from the amplifying circuitry 203 to the calculating function 171 via the attenuator 206. The attenuator 206 attenuates the uncorrected transmission signals extracted by the extracting circuitry 205 when the plurality of the uncorrected transmission signals cannot directly be stored in the buffer 207 due to large amplitude. The buffer 207 outputs the uncorrected transmission signals output by the attenuator 206 to the ADC 204.

When the calculating function 171 according to the modification of the second embodiment acquires the plurality of the uncorrected transmission signals, the plurality of the uncorrected transmission signals passes through the extracting circuitry 205, the attenuator 206, the buffer 207, and the ADC 204. The extracting circuitry 205, the attenuator 206, the buffer 207, and the ADC 204 are also collectively referred to as correcting circuitry. The plurality of the uncorrected transmission signals acquired by the calculating function 171 may contain noise mixed in the course of passing through the correcting circuitry. Thus, the calculating function 171 multiplies the acquired sum component of the uncorrected transmission signals by a conversion function for the correcting circuitry to derive a sum component $\Delta So(t)$ of the uncorrected transmission signals from which the effect of noise mixed in the course of passing through the correcting circuitry is removed. The conversion function for the correcting circuitry is a function that corrects the sum component of the uncorrected transmission signals by considering noise so as to convert the sum component back to the sum component of the uncorrected transmission signals at the point in time when being output from the amplifying circuitry 203, the sum component of the uncorrected transmission signals acquired by the calculating function 171.

After deriving $\Delta So(t)$, the calculating function 171 calculates a correction value in the same manner as the correction value calculating circuitry 2 according to the first embodiment performs.

In the above embodiment, the case is described where the calculating function 171 acquires, as an uncorrected sum component, a sum component of a plurality of uncorrected transmission signals by adding the plurality of the uncorrected transmission signals acquired at a point in time from immediately after generation of the signals to immediately before application of the signals to the transducer element 303 in the ultrasound probe 11a. However, the embodiment is not limited to this case. For example, the calculating function 171 may acquire, as an uncorrected sum component, a sum component of a plurality of uncorrected ultrasound waves by adding the plurality of the uncorrected ultrasound waves acquired at the point in time when the ultrasound probe transmits the ultrasound waves based on the respective uncorrected transmission signals. In this case, the calculating function 171 acquires a sum component of uncorrected ultrasound waves measured by a hydrophone, for example.

In the second embodiment, the case is described where the calculating function 171 is provided in the processing circuitry 170a. However, the embodiment is not limited to this case. For example, calculating circuitry having the same function as the calculating function may be provided in the transmitter circuitry 111a illustrated in FIG. 5 and FIG. 6.

Other Embodiments

The first embodiment and the second embodiment have been described. Embodiments according to the present disclosure, however, can be implemented in various different forms other than the foregoing first and second embodiments.

In the above embodiments, the case is described where two ultrasound waves with a phase of 0 degrees and a phase of 180 degrees, respectively, are transmitted successively. However, the embodiments are not limited to this case. For example, the embodiments are applicable to a case where three ultrasound waves with a phase of 0 degrees, a phase of 120 degrees, and a phase of 240 degrees, respectively, are transmitted successively to remove fundamental components and second harmonic components, thereby extracting only third harmonic components.

Furthermore, for example, a method for THI has been in actual use in which imaging is performed by using second harmonic components and difference sound components contained in reception signals (also referred to as differential THI). The above embodiments are applicable to the imaging method that uses difference sound components. The imaging method that uses difference sound components, for example, causes the ultrasound probe 11 (11a) to transmit transmission ultrasound waves having a composite waveform obtained by combining a first fundamental wave having the center frequency of "f1" and a second fundamental wave having the center frequency of "f2" larger than "f1". The composite waveform is obtained by combining the waveforms of the first and the second fundamental waves having respective phases adjusted to each other so that a difference sound component having the same polarity as that of a second harmonic component is generated. The transmitter circuitry 111 (111a) transmits, for example, two transmission ultrasound waves having the composite waveform successively while inversing the phase of the second wave. In this case, for example, the B-mode processing circuitry 120 adds two reception signals to extract a harmonic component with fundamental components removed and thus mainly containing difference sound components and second harmonic components, and then performs envelope detection processing or other processing.

In the above embodiments, the conversion function is described as a frequency component; however the conversion function may be a time-based function. In this case, a correction value is calculated by multiplying $\Delta So(t)$ by a conversion function that is a time-based function.

The components of the devices and apparatuses illustrated in the drawings described in the above embodiments are functionally conceptual, and do not necessarily need to be configured physically as illustrated in the drawings. That is, the specific forms of distribution or integration of the devices and apparatuses are not limited to those illustrated, and the whole or a part thereof can be configured by being functionally or physically distributed or integrated in any form of units, depending on various types of loads, usage conditions, and the like. Furthermore, the whole of or a part of the various processing functions performed in the respective devices and apparatuses can be implemented by a CPU, and a computer program parsed and executed by the CPU, or implemented as hardware by wired logic.

The control method described in the foregoing embodiments can be implemented by executing a previously prepared control program on a computer such as a personal computer or a workstation (medical image diagnosis apparatus). This control program can be distributed through a network such as the Internet. This control program can also be recorded on a computer-readable recording medium such as a hard disk, a flexible disk (FD), a compact disc read only memory (CD-ROM), a magnetic optical disc (MO), or a digital versatile disc (DVD), and executed by being read out from the recording medium by the computer.

At least one of the embodiments described above can reduce noise in an image of harmonic components generated by transmitting a plurality of ultrasound waves with different phases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   an ultrasound probe that is connected to an apparatus body through a cable and includes an ultrasound transducer element to transmit and receive an ultrasound wave; and
   first circuitry configured to:
      generate transmission waveform data,
      generate, from the transmission waveform data, transmission signals to be transmitted by the ultrasound probe, and
      output the transmission signals to the ultrasound probe through the cable, and
   second circuitry configured to obtain a plurality of uncorrected transmission signals between the cable and the ultrasound transducer element and to calculate a correction value based on a sum component of the obtained plurality of uncorrected transmission signals, the plurality of uncorrected transmission signals being transmitted from the first circuitry through the cable and being obtained before transmitted by the ultrasound probe, wherein
   the ultrasound probe transmits ultrasound waves based upon the transmission signals,
   the first circuitry, when causing the ultrasound probe to transmit a plurality of ultrasound waves with different phases successively depending on a transmission condition after the second circuitry calculates the correction value, generates corrected transmission waveform data based on the calculated correction value, the corrected transmission waveform data causing a value of a sum component of the plurality of ultrasound waves with different phases transmitted successively to be zero, and
   the second circuitry calculates the correction value to correct at least one of noise introduced into the transmission signals by at least one of the first circuitry and the cable and factors introduced into the transmission signals by at least one of the first circuitry and the cable.

2. The ultrasound diagnosis apparatus according to claim 1, wherein the first circuitry generates the transmission waveform data based on a plurality of pieces of uncorrected transmission waveform data, the plurality of pieces of uncorrected transmission waveform data corresponding to a plurality of respective ultrasound waves transmitted successively depending on the transmission condition and causing the sum component to be zero, and based on the calculated correction value that is dependent on the transmission condition.

3. The ultrasound diagnosis apparatus according to claim 2 wherein
   the first circuitry generates the plurality of pieces of uncorrected transmission waveform data and generates a plurality of uncorrected transmission signals corresponding to the respective generated pieces of uncorrected transmission waveform data, and
   the second circuitry acquires, as an uncorrected sum component, a sum component of the obtained plurality of uncorrected transmission signals acquired at a first point in time from immediately after generation of the generated transmission signals to before application of the generated transmission signals to a transducer element in the ultrasound probe, or a sum component of uncorrected ultrasound waves each acquired at a second point in time when the ultrasound probe transmits the ultrasound waves based on the respective generated plurality of uncorrected transmission signals, and the second circuitry calculates the correction value based on the acquired uncorrected sum component.

4. The ultrasound diagnosis apparatus according to claim 3, wherein the second circuitry calculates the correction value based on a conversion component obtained by converting the uncorrected sum component with a conversion function that corrects a waveform at the first point in time or the second point in time by considering noise and the second circuitry converts the waveform back to a waveform of the generated transmission waveform data that has been used to generate the waveform at the first point in time or the second point in time.

5. The ultrasound diagnosis apparatus according to claim 4, wherein
   the conversion function is a conversion function that converts a frequency spectrum of the waveform at the first point in time or the second point in time back to a frequency spectrum of a waveform of transmission waveform data that has been used to generate the waveform at the first point in time or the second point in time, and
   the second circuitry calculates the conversion component from a conversion spectrum calculated from the conversion function and a frequency spectrum obtained by weighting a certain frequency band corresponding to the transmission condition in a frequency spectrum of the uncorrected sum component.

6. The ultrasound diagnosis apparatus according to claim 5, wherein the ultrasound probe further includes extracting circuitry configured to output the plurality of the uncorrected transmission signals transmitted through the cable to the second circuitry, wherein the second circuitry acquires the sum component of the obtained uncorrected transmission signals by adding the obtained plurality of uncorrected transmission signals output by the extracting circuitry.

7. The ultrasound diagnosis apparatus according to claim 5, further comprising:
converting circuitry configured to convert uncorrected transmission waveform data generated by the first circuitry to uncorrected transmission signals and output the converted uncorrected transmission signals to the ultrasound probe; and
extracting circuitry configured to output the converted uncorrected transmission signals output by the converting circuitry to the second circuitry, the converted uncorrected transmission signals being extracted before being output to the ultrasound probe, wherein the second circuitry acquires a sum component of the converted uncorrected transmission signals by adding the converted uncorrected transmission signals output by the extracting circuitry.

8. The ultrasound diagnosis apparatus according to claim 5, wherein the second circuitry acquires the sum component of the uncorrected ultrasound waves by adding a plurality of the uncorrected ultrasound waves measured by a hydrophone.

9. The ultrasound diagnosis apparatus according to claim 4, wherein the ultrasound probe further includes extracting circuitry configured to output the plurality of the uncorrected transmission signals transmitted through the cable to the second circuitry, wherein the second circuitry acquires the sum component of the obtained uncorrected transmission signals by adding the obtained plurality of uncorrected transmission signals output by the extracting circuitry.

10. The ultrasound diagnosis apparatus according to claim 4, further comprising:
converting circuitry configured to convert uncorrected transmission waveform data generated by the first circuitry to uncorrected transmission signals and output the converted uncorrected transmission signals to the ultrasound probe; and
extracting circuitry configured to output the converted uncorrected transmission signals output by the converting circuitry to the second circuitry, the converted uncorrected transmission signals being extracted before being output to the ultrasound probe, wherein the second circuitry acquires a sum component of the converted uncorrected transmission signals by adding the converted uncorrected transmission signals output by the extracting circuitry.

11. The ultrasound diagnosis apparatus according to claim 4, wherein the second circuitry acquires the sum component of the uncorrected ultrasound waves by adding a plurality of the uncorrected ultrasound waves measured by a hydrophone.

12. The ultrasound diagnosis apparatus according to claim 3, wherein the ultrasound probe further includes extracting circuitry configured to output the plurality of the uncorrected transmission signals transmitted through the cable to the second circuitry, wherein the second circuitry acquires the sum component of the obtained plurality of uncorrected transmission signals by adding the obtained plurality of the uncorrected transmission signals output by the extracting circuitry.

13. The ultrasound diagnosis apparatus according to claim 12, wherein the extracting circuitry extracts the plurality of the uncorrected transmission signals output to a certain transducer element among a plurality of transducer elements in the ultrasound probe.

14. The ultrasound diagnosis apparatus according to claim 3, further comprising:
converting circuitry configured to convert uncorrected transmission waveform data generated by the first circuitry to uncorrected transmission signals and output the converted uncorrected transmission signals to the ultrasound probe; and
extracting circuitry configured to output the converted uncorrected transmission signals output by the converting circuitry to the second circuitry, the converted uncorrected transmission signals being extracted before being output to the ultrasound probe, wherein the second circuitry acquires a sum component of the converted uncorrected transmission signals by adding the converted uncorrected transmission signals output by the extracting circuitry.

15. The ultrasound diagnosis apparatus according to claim 14, wherein the extracting circuitry extracts the plurality of the uncorrected transmission signals output to a certain transducer element among a plurality of transducer elements in the ultrasound probe.

16. The ultrasound diagnosis apparatus according to claim 3, wherein the second circuitry acquires the sum component of the uncorrected ultrasound waves by adding a plurality of the uncorrected ultrasound waves measured by a hydrophone.

17. The ultrasound diagnosis apparatus according to claim 1, wherein the second circuitry reports an abnormality when the calculated correction value is outside a certain range.

18. The ultrasound diagnosis apparatus according to claim 1, wherein the first circuitry generates the transmission waveform data by using the obtained plurality of uncorrected transmission signals that have been transmitted through the cable and are detected between the cable and the ultrasound transducer element in the ultrasound probe.

* * * * *